(12) United States Patent
Sellinger et al.

(10) Patent No.: US 11,884,608 B2
(45) Date of Patent: Jan. 30, 2024

(54) DIMERIZATION OF CYCLOPENTADIENE FROM SIDE STREAM FROM DEBUTANIZER

(71) Applicant: KELLOGG BROWN & ROOT LLC, Houston, TX (US)

(72) Inventors: David Sellinger, Houston, TX (US); Robert Choi, Houston, TX (US); Quo-Chen Yeh, Sugar Land, TX (US); Alok Srivastava, Houston, TX (US); Kristine E. Hamilton, Houston, TX (US); Michael A. Radzicki, Houston, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 17/729,968

(22) Filed: Apr. 26, 2022

(65) Prior Publication Data

US 2022/0340501 A1    Oct. 27, 2022

Related U.S. Application Data

(60) Provisional application No. 63/180,282, filed on Apr. 27, 2021.

(51) Int. Cl.
*C07C 2/38* (2006.01)
*B01J 19/00* (2006.01)
(Continued)

(52) U.S. Cl.
CPC ............. *C07C 2/38* (2013.01); *B01J 19/0013* (2013.01); *C07C 7/04* (2013.01); *C07C 13/61* (2013.01);
(Continued)

(58) Field of Classification Search
CPC .. C07C 2/38; C07C 7/04; C07C 13/61; C07C 2603/68; B01J 19/0013; B01J 2219/00051
See application file for complete search history.

(56) References Cited

U.S. PATENT DOCUMENTS

| 4,802,978 A | 2/1989 | Schmit et al. |
| 4,831,200 A | 5/1989 | Debras et al. |

(Continued)

FOREIGN PATENT DOCUMENTS

| GB | 907087 A | 10/1962 |
| RU | 2581061 C1 * | 4/2016 |

OTHER PUBLICATIONS

Xu, R et al., "Cyclopentadiene Dimerization Kinetics in the Presence of C5 Alkenes and Alkadienes," pates 22516-22525, Industrial and Engineering Chemistry Research, vol. 58. Sep. 5, 2019; Entire Document; DOI: 10.1021/acs.iecr.9b04018.

(Continued)

*Primary Examiner* — Thuan D Dang
(74) *Attorney, Agent, or Firm* — Gary M. Machetta

(57) ABSTRACT

A system and a process for dimerizing cyclopentadiene (CPD) including producing a $C_6+C_7$ rich bottoms stream and a $C_5$ rich side draw from a debutanizer, where the $C_5$ rich side draw and at least a portion of the $C_6+C_7$ rich bottoms stream are directed to a dimerizer where the CPD is thermally dimerized to dicyclopentadiene (DCPD). DCPD is more stable than CPD and thus safer to handle.

6 Claims, 1 Drawing Sheet

(51) Int. Cl.
*C07C 13/61* (2006.01)
*C07C 7/04* (2006.01)

(52) U.S. Cl.
CPC . *B01J 2219/00051* (2013.01); *C07C 2603/68* (2017.05)

(56) References Cited

U.S. PATENT DOCUMENTS

| | | | |
|---|---|---|---|
| 5,090,977 | A | 2/1992 | Strack et al. |
| 5,877,363 | A | 3/1999 | Gildert et al. |
| 6,258,989 | B1 | 7/2001 | Owen et al. |
| 6,420,619 | B1 | 7/2002 | Gartside et al. |
| 6,576,132 | B2 | 6/2003 | Kurukchi et al. |
| 7,128,827 | B2 | 10/2006 | Tallman et al. |
| 7,294,749 | B2 | 11/2007 | Verma et al. |
| 7,527,725 | B2 | 5/2009 | Viswanathan et al. |
| 7,560,019 | B2 | 7/2009 | McCoy et al. |
| 7,741,526 | B2 | 6/2010 | Kuechler et al. |
| 8,025,773 | B2 | 9/2011 | McCoy et al. |
| 9,896,395 | B2 | 2/2018 | Iaccino et al. |
| 9,969,944 | B2 | 5/2018 | Kurukchi et al. |
| 10,619,112 | B2 | 4/2020 | Al-Ghamdi |
| 2002/0128528 | A1 | 9/2002 | Pinault et al. |
| 2006/0025641 | A1 | 2/2006 | Gartside et al. |
| 2007/0264176 | A1 | 11/2007 | Stewart et al. |
| 2015/0175502 | A1* | 6/2015 | Hwang ............ C07C 2/50 585/312 |

OTHER PUBLICATIONS

Gao, S. et al., "The reaction kinetics of cyclopentadiene dimerizaiton using differential scanning calorimetry: Experiments and modelling" pp. 241-246, Thermochimica Acta. vol. 589. Aug. 10, 2014; Entire Document; DOI: 10.1016/j.tca2014.05.031.

Yang, Z et al., "Molecular dynamics of the two-stage mechanism of cyclopentadiene dimerization: concerted or stepwise?" pp. 120-125. Chemical Physics. vol. 514. Oct. 25, 2018; Entire Document; DOI: 10.1016/j.chemphys.2018.02.020.

Patent Cooperation Treaty, "International Search Report and Written Opinion" dated Jul. 25, 2022 for International Application No. PCT/US2022/026537 filed Apr. 27, 2022, 7 pages.

* cited by examiner

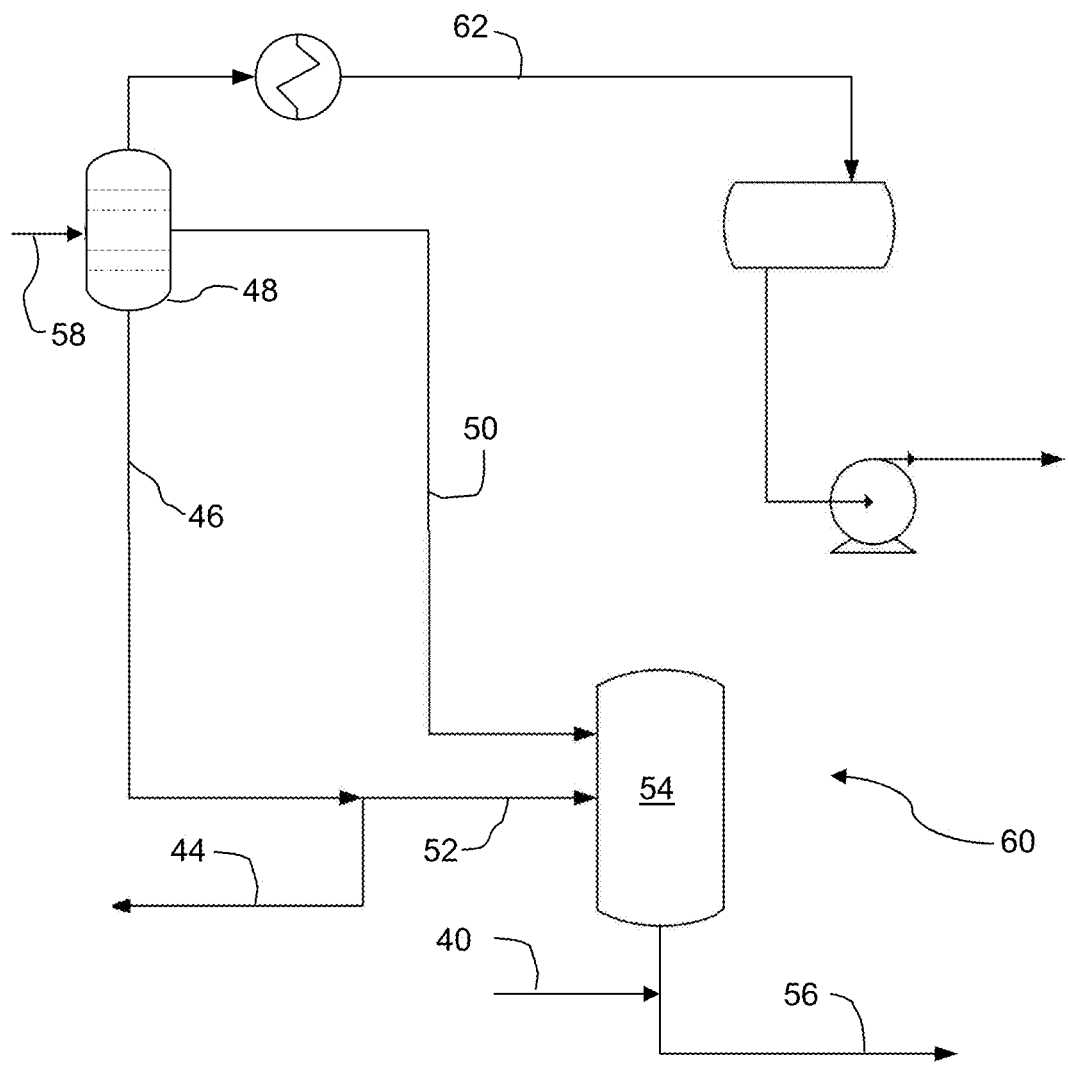

DIMERIZATION OF CYCLOPENTADIENE FROM SIDE STREAM FROM DEBUTANIZER

CROSS REFERENCE TO RELATED APPLICATION

This application claims priority to U.S. Provisional Patent Application having Ser. No. 63/180,282 filed on Apr. 27, 2021 which is incorporated by reference herein.

TECHNICAL FIELD

The present invention relates to a system and a process for indigenously dimerizing cyclopentadiene (CPD), and more particularly relates to dimerizing CPD to give dicyclopentadiene (DCPD) in an ethylene plant.

BACKGROUND

Steam cracking, also referred to as pyrolysis, is the principal process used to produce lighter alkenes (e.g. ethylene), commonly known as olefins, from a naphtha, liquefied petroleum gas (LPG), ethane, propane, and/or butane feedstock.

In a conventional steam cracking process, a gaseous or liquid hydrocarbon feed like naphtha, LPG, or ethane is diluted with steam and briefly heated in a furnace without the presence of oxygen. The cracked gas products produced in the reaction depend on the composition of the feed, the hydrocarbon-to-steam ratio, and on the cracking temperature and furnace residence time. Light hydrocarbon feeds, such as ethane, LPGs, or light naphtha, give cracked gas streams rich in the lighter alkenes, including ethylene, propylene, and butadiene. Heavier hydrocarbons (full range and heavy naphthas as well as other refinery products) additionally yield products rich in aromatic hydrocarbons and hydrocarbons suitable for inclusion in gasoline or fuel oil, such as a $C_{5+}$ pyrolysis gasoline stream leaving the bottom of a debutanizer tower used in the olefin plant for separating heavier hydrocarbons in the cracked gas stream from $C_4$ hydrocarbons. This pyrolysis gasoline stream usually contains $C_5$ diolefins, mainly cyclopentadienes, that may then be dimerized to make more stable dicyclopentadienes.

Normally in a steam cracking process, where required, a dimerizer is installed on the bottom stream of debutanizer where $C_5$ diolefins—mainly cyclopentadienes—are dimerized to make more stable dicyclopentadienes. This could be done either to make adhesives and other products from the dicyclopentadienes or simply to transport and store safely the $C_5$-containing pyrolysis gasoline product.

U.S. Pat. No. 6,258,989 B1 discloses dimerizing a stream comprising $C_5$ olefins, $C_5$ diolefins, CPD, DCPD, and aromatics mixture of benzene, toluene, xylene (BTX) and then separating $C_5$, $C_6$-$C_9$ and $C_{10+}$ for upgrading the molecules. This dimerization is done on a debutanized pyrolysis gasoline stream from a steam cracker. More specifically, U.S. Pat. No. 6,258,989 discloses that a hydrocarbon feedstock containing $C_5$ olefins, $C_5$ diolefins, CPD, DCPD, and aromatics is processed by the steps of heating a hydrocarbon feedstock containing CPD, DCPD, $C_5$ diolefins, benzene, toluene, and xylene in a heating zone, to dimerize CPD to DCPD, thereby forming a first effluent; separating the first effluent into a $C_{6+}$ stream and a $C_5$ diolefin stream; separating the $C_{6+}$ stream into a $C_6$-$C_9$ stream and a $C_{10+}$ stream; separating the $C_{10+}$ stream into a fuel oil stream and a DCPD stream; and hydrotreating the $C_6$-$C_9$ stream to thereby form a BTX stream. In an alternate embodiment, the hydrocarbon feedstock is processed by the steps of heating the hydrocarbon feedstock in a heating zone, to dimerize CPD to DCPD, thereby forming a first effluent; separating the first effluent into a $C_5$-$C_9$ stream and a $C_{10+}$ stream; separating the $C_{10+}$ stream into a fuel oil stream and a DCPD stream; contacting the $C_5$-$C_9$ stream with a selective hydrogenation catalyst, in a first reaction zone and in the presence of hydrogen, to hydrogenate at least a portion of the diolefins, alkynes, and styrene contained in the $C_5$-$C_9$ stream, thereby forming a second effluent; separating the second effluent into a $C_6$-$C_9$ stream and a $C_5$ olefin stream; and contacting the $C_6$-$C_9$ stream with a hydrodesulfurization catalyst, in a second reaction zone and in the presence of hydrogen, to desulfurize at least a portion of the sulfur-containing compounds contained in the $C_6$-$C_9$ stream thereby forming a BTX stream.

In a related process and system, a debutanizer and a dimerizer produce a $C_6$-$C_7$-rich, $C_5$-free stream that used for making up a solvent for a tar solvation quench system. This provides a unique opportunity for processing CPD.

SUMMARY

There is provided, in one non-limiting embodiment, a system for dimerizing cyclopentadiene (CPD), where the system includes a debutanizer that in turn includes a feed of $C_4$-$C_7$ hydrocarbons, a $C_4$ overhead stream, a $C_6$+$C_7$ rich bottoms stream, and a $C_5$ rich side draw, which system also includes a dimerizer that in turn includes a feed from the $C_5$ rich side draw, a feed from at least a portion of the $C_6$+$C_7$ rich bottoms stream, and a pyrolysis gasoline bottoms product stream.

There is also provided, in a different, non-restrictive version, a process for dimerizing cyclopentadiene (CPD), where the process includes introducing a $C_3$-$C_7$ hydrocarbons stream to a debutanizer, debutanizing the $C_3$-$C_7$ hydrocarbons thereby producing a $C_3$+$C_4$ overhead stream, a $C_6$+$C_7$ rich bottoms stream, and a $C_5$ rich side draw, where the process further includes introducing the $C_5$ rich side draw and at least a portion of the $C_6$+$C_7$ rich bottoms stream to a dimerizer, dimerizing the CPD in the dimerizer, and producing a bottoms product stream.

In another non-limiting embodiment there is provided an ethylene plant that includes a system for dimerizing cyclopentadiene (CPD) as described above.

BRIEF DESCRIPTION OF THE DRAWINGS

FIG. 1 is a schematic illustration a process for dimerizing cyclopentadiene (CPD), and more particularly relates to dimerizing CPD to give dicyclopentadiene (DCPD) in an ethylene plant

DETAILED DESCRIPTION

The hydrocarbon feed 58 to debutanizer column 48 is may include $C_3$ or $C_4$ to $C_7$ hydrocarbons. Since streams $C_6$-$C_7$ rich bottoms stream 46, $C_5$-rich side draw stream 50, and overhead stream 62 contain $C_3$-$C_7$ hydrocarbons collectively, hydrocarbon feed 58 should contain $C_4$-$C_7$ hydrocarbons and may also contain $C_3$.

Referring again to the non-limiting embodiment of the cyclopentadiene (CPD) dimerization system 60 and process shown in FIG. 1, the debutanizer column 48 is configured to produce a $C_5$-rich side draw stream 50. The operating conditions of the debutanizer column 48 include an overhead pressure of from about 29 psia (200 kPa) independently to about 130 psia (896 kPa) depending on condensing media (i.e., refrigerant, cooling water); and an overhead operating temperature ranging from about 1° F.(−17° C.) independently to about 113° F. (45° C.); and a bottoms temperature from about 180° F. (82° C.) independently to about 280° F. (138° C.).

It will be appreciated that the location of $C_5$-rich side draw stream 50 should be carefully evaluated through simulation of the debutanizer column 48 to ensure that the $C_5$-rich side draw stream 50 has the highest concentration of $C_5$ range hydrocarbons in order to minimize the amount of $C_5$ range hydrocarbons concentration in $C_6$-$C_7$ rich bottoms stream 46 of debutanizer column 48. In accordance with this non-limiting embodiment, the $C_6$-$C_7$ rich bottoms stream 46 of debutanizer column 48 mainly consists of $C_6$+$C_7$ range hydrocarbons.

After drawing any necessary makeup for the optional $C_6$-$C_7$ rich tar solvent makeup stream 44, the net debutanizer bottoms stream 52 may be mixed with the $C_5$-rich side draw stream 50 as feed to a thermal dimerizer 54. The thermal dimerizer 54 may be utilized to dimerize the cyclopentadienes present in the $C_5$-rich side draw stream 50 and any present in the portion of the $C_6$-$C_7$ rich bottoms stream 46 directed to the net debutanizer bottoms stream 52 to dimerize CPD to dicyclopentadiene. This configuration may help to ensure that the combined dimerized pyrolysis gasoline 56 is stabilized to prevent safety hazards in transportation and storage. Any $C_6$-$C_7$ molecules from aromatic rich bottoms stream 46 not used or any surplus molecules are blended with dimerized pyrolysis gasoline 56.

In one non-limiting embodiment, the dimerizer 54 is a thermal dimerizer. The operating conditions of the thermal dimerizer 54 include a pressure of from about 35 psia (241 kPa) independently to about 60 psia (414 kPa); alternatively from about 40 psia (276 kPa) independently to about 50 psia (345 kPa); and an operating temperature ranging from about 200° F. (93° C.) independently to about 250° F. (121° C.); alternatively from about 210° F. (99° C.) independently to about 220° F. (104° C.).

The dimerized pyrolysis gasoline 56 may be further processed to make adhesion products, resins, inks, paints, and the like. Optionally, a $C_8$-$C_{10}$ steam cracked naphtha (SCN) stream 40 may be combined with dimerized pyrolysis gasoline 56.

In the foregoing specification, the invention has been described with reference to specific embodiments thereof. However, the specification is to be regarded in an illustrative rather than a restrictive sense. For example, debutanizer conditions and configuration, dimerizer conditions and configuration, and the composition and amount of the various hydrocarbon streams falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. For instance, in one non-limiting embodiment there may be provided There may be additionally provided, in another non-restrictive version, a process for dimerizing cyclopentadiene (CPD), where the process comprises, consists essentially of, or consists of introducing a $C_4$-$C_7$ hydrocarbons stream to a debutanizer, debutanizing the $C_4$-$C_7$ hydrocarbons thereby producing a $C_4$ overhead stream, a $C_6$-$C_7$ rich bottoms stream, and a $C_5$ rich side draw, where the process further comprises, consists essentially of, or consists of introducing the $C_5$ rich side draw and at least a portion of the $C_6$+$C_7$ rich bottoms stream to a dimerizer, dimerizing the CPD in the dimerizer, and producing a bottoms product stream.

There may also be provided an ethylene plant comprising a system for dimerizing cyclopentadiene (CPD), where the system comprises, consists essentially of, or consists of a debutanizer that in turn comprises, consists essentially of, or consists of a feed of $C_4$-$C_7$ hydrocarbons, a $C_4$ overhead stream, a $C_6$+$C_7$ rich bottoms stream, and a $C_5$ rich side draw, where the system additionally comprises, consists essentially of, or consists of a dimerizer that in turn comprises, consists essentially of, or consists of a feed from the $C_5$ rich side draw, a feed from at least a portion of the $C_6$+$C_7$ rich bottoms stream, and a pyrolysis gasoline bottoms product stream.

The words "comprising" and "comprises" as used throughout the claims, are to be interpreted to mean "including but not limited to" and "includes but not limited to", respectively.

To the extent used herein, the word "substantially" shall mean "being largely but not wholly that which is specified."

As used herein, the singular forms "a," "an," and "the" are intended to include the plural forms as well, unless the context clearly indicates otherwise.

To the extent used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

What is claimed is:

1. A system for dimerizing cyclopentadiene (CPD), the system comprising:
    a debutanizer comprising:
    a feed of $C_4$-$C_7$ hydrocarbons;
    a $C_4$ hydrocarbons overhead stream;
    a $C_6$+$C_7$ hydrocarbons rich bottoms stream; and
    a $C_5$ hydrocarbons rich side draw comprising cyclopentadiene; and
    a dimerizer comprising:
    a feed from the $C_5$ hydrocarbons rich side draw comprising cyclopentadiene;
    a feed from at least a portion of the $C_6$+$C_7$ hydrocarbons rich bottoms stream;
    and a pyrolysis gasoline bottoms product stream.

2. The system of claim 1, wherein the dimerizer is a thermal dimerizer.

3. The system of claim 1, wherein a $C_6$-$C_7$ hydrocarbons rich tar solvent makeup stream is drawn from the $C_6$+$C_7$ hydrocarbons rich bottoms stream and a balance of the $C_6$+$C_7$ hydrocarbons rich bottoms stream is directed to the dimerizer.

4. An ethylene plant comprising:
    A system for dimerizing cyclopentadiene (CPD), the system comprising:
    a debutanizer comprising:
    a feed of $C_4$-$C_7$ hydrocarbons;
    a $C_4$ hydrocarbons overhead stream;
    a $C_6$+$C_7$ hydrocarbons rich bottoms stream; and
    a $C_5$ hydrocarbons rich side draw comprising cyclopentadiene; and
    a dimerizer comprising:
    a feed from the $C_5$ hydrocarbons rich side draw comprising cyclopentadiene;
    a feed from at least a portion of the $C_6$+$C_7$ hydrocarbons rich bottoms stream;
    and a pyrolysis gasoline bottoms product stream.

5. The ethylene plant of claim 4, wherein the dimerizer is a thermal dimerizer.

6. The ethylene plant of claim 4, wherein a $C_6$-$C_7$ hydrocarbons rich tar solvent makeup stream is drawn from the $C_6$+$C_7$ hydrocarbons rich bottoms stream and a balance of the $C_6$+$C_7$ hydrocarbons rich bottoms stream is directed to the dimerizer.

\* \* \* \* \*